US008661872B2

(12) United States Patent
Brocker

(10) Patent No.: US 8,661,872 B2
(45) Date of Patent: Mar. 4, 2014

(54) TEST SYSTEM

(76) Inventor: William J. Brocker, Minnetonka, MN (US)

(*) Notice: Subject to any disclaimer, the term of this patent is extended or adjusted under 35 U.S.C. 154(b) by 553 days.

(21) Appl. No.: 12/927,319

(22) Filed: Nov. 12, 2010

(65) Prior Publication Data

US 2012/0118038 A1 May 17, 2012

(51) Int. Cl.
*G01N 25/00* (2006.01)
*G01P 21/00* (2006.01)
*G01C 25/00* (2006.01)

(52) U.S. Cl.
CPC .............. *G01C 25/005* (2013.01); *G01P 21/00* (2013.01); *G01N 25/00* (2013.01)
USPC .............................. 73/1.38; 73/865.6; 374/45

(58) Field of Classification Search
CPC ...... G01C 25/00; G01C 25/005; G01P 21/00; G01N 25/00
USPC .............. 73/1.37–1.38, 118.01, 865.3, 865.6, 73/866.4; 374/45, 57
See application file for complete search history.

(56) References Cited

U.S. PATENT DOCUMENTS 3,064,364 A * 11/1962 Schueller ................. 73/865.6 X
3,570,315 A * 3/1971 Likeness et al. ............ 73/865.6
4,188,816 A 2/1980 Mairson
4,871,965 A 10/1989 Elbert et al.
5,353,642 A 10/1994 Hasegawa et al.
5,356,365 A 10/1994 Brierton
5,392,631 A * 2/1995 Elwell ...................... 73/865.6 X
5,813,541 A 9/1998 Mottram
6,227,701 B1 5/2001 Wu
6,820,503 B2 11/2004 Sueyoshi et al.
8,007,166 B2 * 8/2011 Abbink et al. ............. 374/45 X
2005/0269308 A1 12/2005 Allgeyer
2007/0204672 A1 9/2007 Huang et al.
2007/0295114 A1 12/2007 Pilcher et al.
2009/0249899 A1 10/2009 Wong et al.

* cited by examiner

*Primary Examiner* — Thomas P Noland

(74) *Attorney, Agent, or Firm* — Kinney & Lange, P.A.

(57) ABSTRACT

A testing system tests or calibrates an electronic test subject while rotating the test subject within a thermally controlled chamber. The testing system includes a stationary thermal chamber, a test subject, testing electronics that receive electronic data from the test subject, and a rotating platform inside the thermal chamber to which both the test subject and the testing electronics are mounted. The testing system further includes a platform cover for the rotatable platform that rotates with the rotatable platform, and exposes the test subject to the temperature inside the thermal chamber and insulates the testing electronics from the temperature inside the thermal chamber.

20 Claims, 9 Drawing Sheets

10 30 14 28 32 16 T 42 36 38 12 22 44 24C 24B 40 34 24D 24A 18 26 20

TEST SYSTEM

BACKGROUND

The present invention relates to thermal testing of devices that are being rotated, and more particularly, to testing, calibration, or characterization of angular velocity or acceleration sensors that are being rotated within a thermal chamber.

Many modern electronic devices contain angular velocity and/or acceleration sensors, including aircraft control systems, navigation systems, cell phones, and portable personal computers. These sensors need to be developed, tested, calibrated, and characterized prior to implementation in these devices. Because many of these devices are used in varying climates, the characteristics of the sensors should be measured over a range of temperatures. Also, many of these devices are used for long time periods, over which the sensors can change, so time-based characteristics should also be measured. This testing can be done using a thermal chamber that rotates, but thermal chambers can be so massive that it can be dangerous and expensive to perform testing at even moderate angular velocities.

SUMMARY

According to the present invention, a testing system tests or calibrates an electronic test subject while rotating the test subject within a thermally controlled chamber. The testing system includes a stationary thermal chamber, a test subject, testing electronics that receive electronic data from the test subject, and a rotating platform inside the thermal chamber to which both the test subject and the testing electronics are mounted. The testing system further includes a platform cover for the rotatable platform that rotates with the rotatable platform, and exposes the test subject to the temperature inside the thermal chamber and insulates the testing electronics from the temperature inside the thermal chamber.

Another embodiment is a method of operating a testing system. The method includes controlling the temperature inside a thermal chamber, positioning a test subject on a rotating platform inside the thermal chamber, rotating the platform, testing the test subject using testing electronics that are also positioned on the platform, and insulating thermally the testing electronics from the thermal chamber.

DETAILED DESCRIPTION

Figure 1:
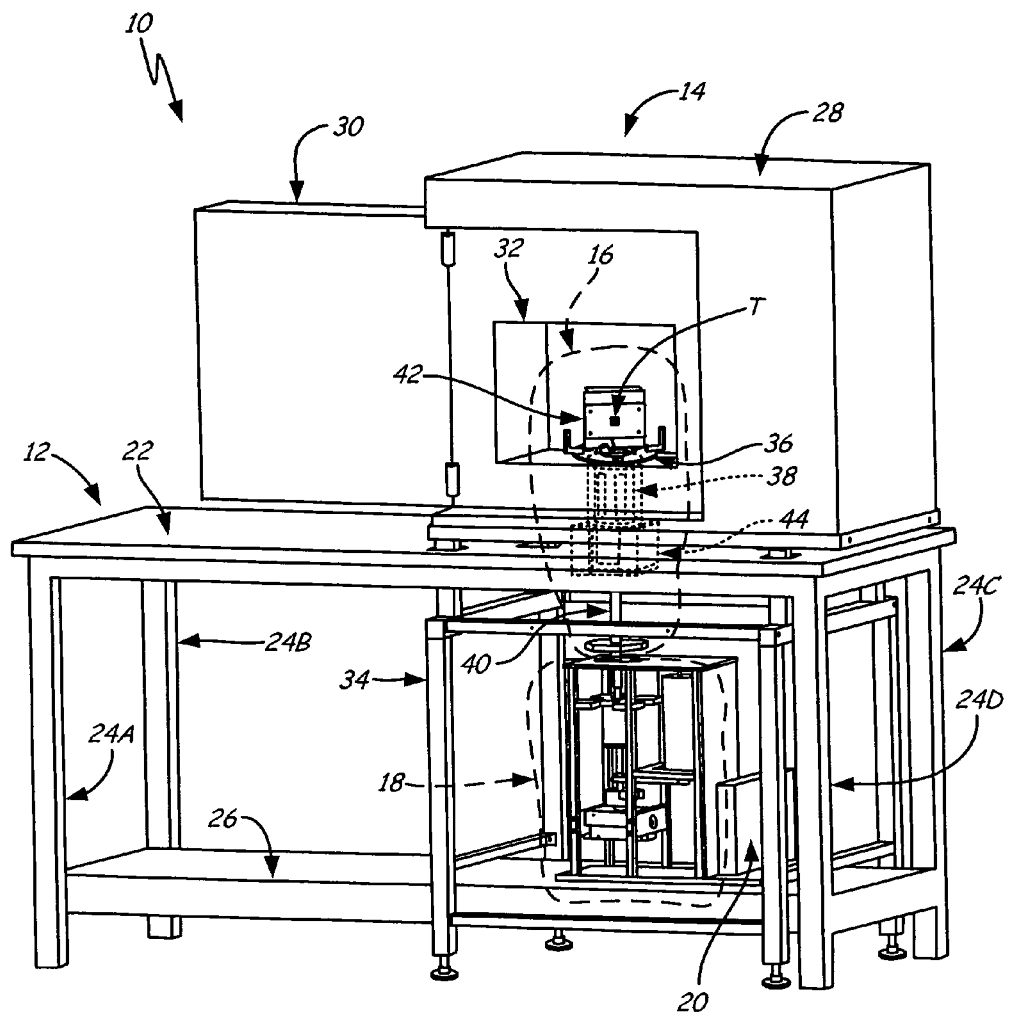
FIG. 1 is a perspective view showing a thermal testing assembly for rotating a test subject in a thermal chamber.

In FIG. 1, thermal testing assembly 10 for testing of test subject T under various temperature and rotational conditions is shown in perspective view. Thermal testing assembly 10 includes bench 12, thermal chamber 14, upper assembly 16, lower assembly 18, and testing controller 20. Bench 12 includes bench top 22, bench legs 24A-24D, and bench shelf 26. Thermal chamber 14 includes thermal housing 28, thermal door 30, and thermal cavity 32, and is supported by thermal chamber frame 34. Upper assembly 16 includes platform 36, platform spacer 38, first hollow shaft 40, testing electronics 42, and platform motor 44.

Thermal chamber 14 is supported in a stationary position by thermal chamber frame 34, which also isolates thermal chamber 14 from any vibrations associated with the rest of thermal testing assembly 10. Thermal chamber 14 is shown with thermal door 30 in the open position. Thermal door 30 is mounted on hinges and can be opened in order to access thermal cavity 32. Thermal door 30 can be shut, and, in conjunction with thermal housing 28, a closed environment is created inside thermal cavity 32, the temperature of which can be controlled over a wide range.

Bench 12 provides a rigid frame to which upper assembly 16 and lower assembly 18 are mounted. Specifically, lower assembly 18 is attached to bench shelf 26. Upper assembly 16, particularly platform motor 44, is attached to bench top 22, and bench top 22 is supported by bench legs 24A-24D.

Upper assembly 16 has platform motor 44 which is connected to first hollow shaft 40, platform spacer 38, and platform 36. Platform motor 44 is outside and below thermal chamber 14, while platform spacer 38 passes through an aperture in the bottom of thermal housing 28. Platform spacer 38 is connected at its upper end to platform 36, which is inside thermal cavity 32. Platform 36 supports testing electronics 42, with test subject T being physically attached and electrically connected to testing electronics 42.

In the illustrated embodiment, platform motor 44 is a permanent magnet electric motor having permanent magnets on its rotor and windings on its stator. Platform motor 44 is non-contact and brushless, with the rotor being supported by an air bearing. Platform motor 44 rotates first hollow shaft 40, platform spacer 38, platform 36, testing electronics 42, and test subject T.

Test subject T can be any type of electronic device. Specifically, test subject T can comprise an inertial measurement unit. More specifically, test subject T can comprise a device or sensor for measuring angular velocity or acceleration, for example, a gyroscope or an accelerometer. In order to characterize, calibrate, and/or test such a device at various temperatures, test subject T is rotated inside thermal cavity 32 at controlled speeds. Such rotation puts a controlled rate or force on test subject T, and the response to that rate or force can be measured.

In order to carry out the testing, calibrating, or characterizing of test subject T, pneumatic, electrical, and communication lines are required. For example, test subject T is mounted on and electrically connected to testing electronics 42. This connection allows for testing to be accomplished within thermal chamber 14 without requiring raw signals to be passed farther than testing electronics 42. Both test subject T and testing electronics 42 require electrical power in order to operate, and the data and results of the testing done by testing electronics 42 must be sent and received by testing controller 20. In addition, communication can occur in the opposite direction, wherein testing controller 20 can download initialization and configuration data into testing electronics 42 and test subject T. Because testing controller 20 is a stationary device, any wire or cable that runs between testing electronics 42 and testing controller 20 must run down first hollow shaft 40 to lower assembly 18. Lower assembly 18 has rotary couplings for the electrical and communication lines to allow for testing controller 20 to be stationary while testing electronics 42 are rotating. Due to the rotation of components in upper assembly 16 and the lines connecting upper assembly 16 and lower assembly 18, there are rotating components in lower assembly 18 that are substantially rotationally synchronized and substantially coaxial with the rotating components in upper assembly 16.

While test subject T must be exposed to the temperature extremes inside thermal cavity 32, such exposure can be problematic for testing electronics 42. Therefore, there is a housing or shroud for testing electronics 42 (as shown later in FIG. 6A-6B) that thermally insulates testing electronics 42 from the temperatures in thermal cavity 32. That shroud receives air from an external supply in order to maintain testing electronics 42 within standard operating temperatures. Similarly to the electrical and communication lines, the pneumatic line runs down first hollow shaft 40 to lower assembly 18 where there is a rotary connection to an air source.

The components and configuration of thermal testing assembly 10 allow for rotational testing of test subject T inside thermal chamber 14, with thermal chamber 14 being stationary. Having testing electronics 42 attached to test subject T allows for output signals from test subject T to be processed immediately. That means that the raw output signal is not degraded by being passed out of upper assembly 16 and through lower assembly 18 prior to being signal processed. In addition, the insulating housing and pneumatic temperature control of testing electronics 42 protects testing electronics 42 from temperature extremes. Also, having the rotary connections on lower assembly 18 minimizes the amount of equipment attached to upper assembly 16. This minimizes the force and vibrations in upper assembly 16, which increases the fidelity of the testing results and minimizes the maintenance required for upper assembly 16.

Depicted in FIG. 1 is one embodiment of the present invention, to which there are alternative embodiments. For example, there can be multiple test subjects T mounted on testing electronics 42. For another example, test subject T can be offset from testing electronics 42 in order to create a longer moment arm, which magnifies the force put on test subject T when testing electronics 42 is rotated. For another example, upper assembly 16 and lower assembly 18 can be oriented horizontally, such that upper assembly 16 enters thermal chamber 14 through an aperture in the side of thermal housing 28.

Figure 2:
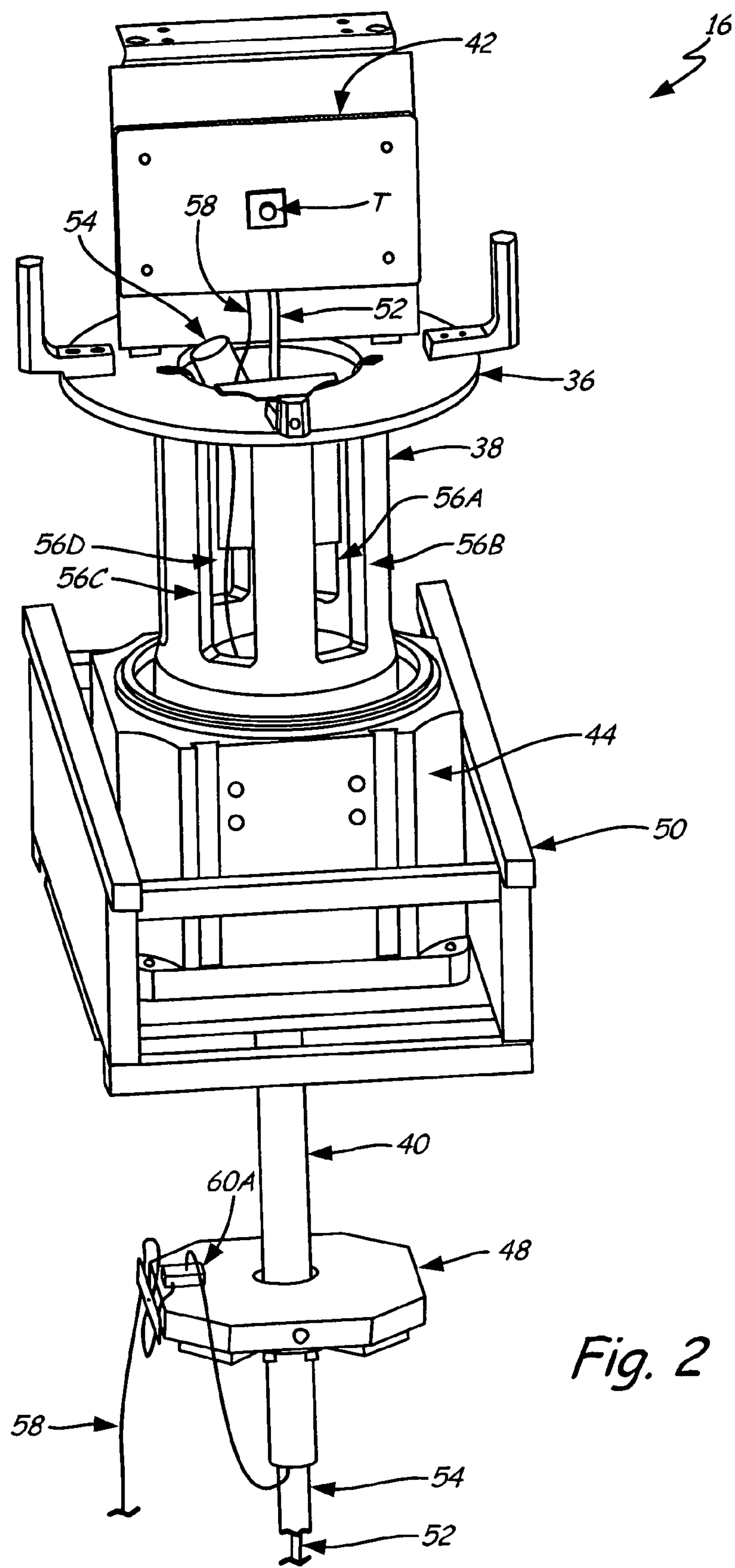
FIG. 2 is an enlarged perspective view of an upper assembly of the thermal testing assembly of FIG. 1.

In FIG. 2, upper assembly 16 of thermal testing assembly 10 is shown in perspective view. Shown in FIG. 2 is platform 36, platform spacer 38, first hollow shaft 40, testing electronics 42, platform motor 44, counterbalance 48, platform motor mount 50, fiber optic cable 52, air distribution tube 54, air vents 56A-56D, slip ring wires 58, terminal block 60A, and test subject T. However as with FIG. 1, there is a housing or shroud for testing electronics 42 (as shown later in FIG. 6A-6B) that is not shown in FIG. 2.

As stated previously, upper assembly 16 is supported by bench 12. Specifically, platform motor 44 has platform motor mount 50 which is attached to bench 12. Attached to the top of rotor of platform motor 44 is platform spacer 38, platform 36, and testing electronics 42. Also attached to the center of rotor of platform motor 44 is first hollow shaft 40, which projects through an aperture in the bottom of platform motor 44. Attached to first hollow shaft 40 is counterbalance 48 with air distribution tube 54 being situated within first hollow shaft 40.

At the top of upper assembly 16, test subject T is electrically connected to testing electronics 42, and testing electronics 42 is electrically connected to slip ring wires 58 (which are depicted as a single wire for simplicity). Slip ring wires 58 run down through the centers of platform 36, platform spacer 38, the rotor of platform motor 44, and first hollow shaft 40. Slip ring wires 58 exit platform motor 44 through the bottom of first hollow shaft alongside air distribution tube 54. Slip ring wires 58 are attached to terminal block 60A and counterbalance 48 before being routed to lower assembly 18. Slip ring wires 58 are a conduit for electrical power from lower assembly 18 to testing electronics 42.

Testing electronics 42 is optically connected to fiber optic cable 52. Fiber optic cable 52 runs down and enters air distribution tube 54 though an aperture. Then fiber optic cable 52 runs through the centers of first hollow shaft 40 and air distribution tube 54 in order to reach lower assembly 18. Fiber optic cable 52 is an optical conduit for communication between testing electronics 42 and testing controller 20.

The top end of air distribution tube 54 is located near testing electronics 42. As shown in FIG. 3B, the bottom end of air distribution tube 54 is attached to lower assembly 18. Air distribution tube 54 forms a pathway that can be a pneumatic conduit for air from lower assembly to reach testing electronics 42. Because of a shroud over platform 36 (as shown later in FIG. 6A-6B), this air cannot reach thermal cavity 32. Instead, the air is directed downward past air distribution tube 54 and out through air vents 56A-56D in platform spacer 38. Air vents 56A-56D allow the air to flow down between platform spacer 38 and the aperture in bench 12 so that the air can be vented to the atmosphere around thermal testing assembly 10.

Counterbalance 48 also provides a weight to balance platform motor 44, given that there are many other components attached to platform motor 44, such as platform 36 and testing electronics 42. This allows for the correct center of gravity to be achieved in order for the air bearing rotor in platform motor 44 to operate smoothly and safely. In addition it would also be advantageous for platform motor 44 to be precision aligned such that no unnecessary motion is imparted to test subject T when platform 36 is rotated.

The components and configuration of upper assembly 16 allow for air, electricity, and communications to be routed up to testing electronics 42. The air allows for testing electronics 42 to be maintained within standard operating temperatures. This can occur because the air being delivered to testing electronics 42 can have a temperature that is independent from that in thermal cavity 32. Therefore, test subject T can be tested, calibrated, or characterized at varying temperatures without the varying temperature affecting testing electronics 42.

The electrical connection between testing electronics 42 and test subject T allows for electrical power to reach test subject T and for the raw output from test subject T to be processed by testing electronics 42. The electrical/optical connection between testing electronics 42 and testing controller 20 allows for a wide bandwidth of processed data to be passed regarding the output from test subject T. Such transmission can occur because testing electronics 42 can communicate electrically (to test subject T) and optically (to testing controller 20).

Besides the primary function of counterbalance 48 as stated previously, counterbalance 48 has further purposes. For example, terminal block 60A is attached to counterbalance 48 in order to ease the replacement of electrical components, such as testing electronics 42, without requiring complete rewiring of thermal testing assembly 10. Another example is that the attachment of slip ring wires 58 on counterbalance 48 provides friction in case slip ring wires 58 are pulled. In the event that both platform motor 44 and slip ring motor 62 (shown in FIGS. 3A and 3B) lose power while rotating, platform motor 44 and slip ring motor 62 may decelerate at different rates. This would cause slip ring wires 58 to wrap around air distribution tube 54 and/or second hollow shaft 64 (shown in FIGS. 3A and 3B) and after sufficient wrapping, slip ring wires 58 would be pulled until they are disconnected. The friction caused by the connection of slip ring wires 58 to counterbalance 48 assists in equalizing the respective rotational speeds and deceleration rates of platform motor 44 and slip ring motor 62. Therefore, it can be advantageous to provide extra length for slip ring wires 58 to provide sufficient friction.

Depicted in FIG. 2 is one embodiment of the present invention, to which there are alternative embodiments. For example, nitrogen or a noble gas can be used instead of air. For another example, while this end of air distribution tube 54 is depicted as an open-ended tube, one skilled in the art can appreciate that air distribution tube 54 can be a manifold with a plurality of openings. The openings can also have additional tubing emerging therefrom, such that air can be directed to specific locations, for example, on testing electronics 42. For a further example, slip ring wires 58 can also transmit data or digital signals at a low data rate as well as transmitting electrical power.

Figure 3A:
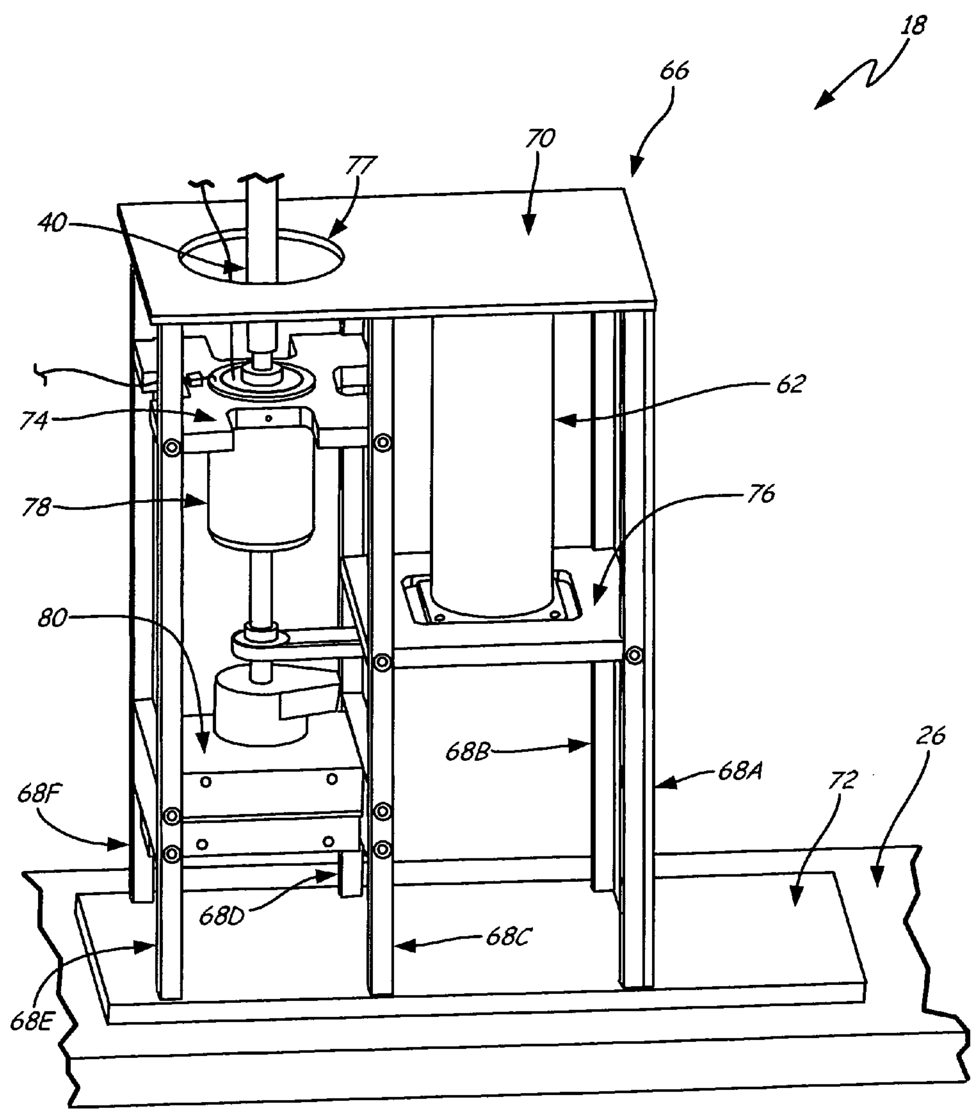
FIG. 3A is an enlarged perspective view of a lower assembly of the thermal testing assembly of FIG. 1.
Figure 3B:
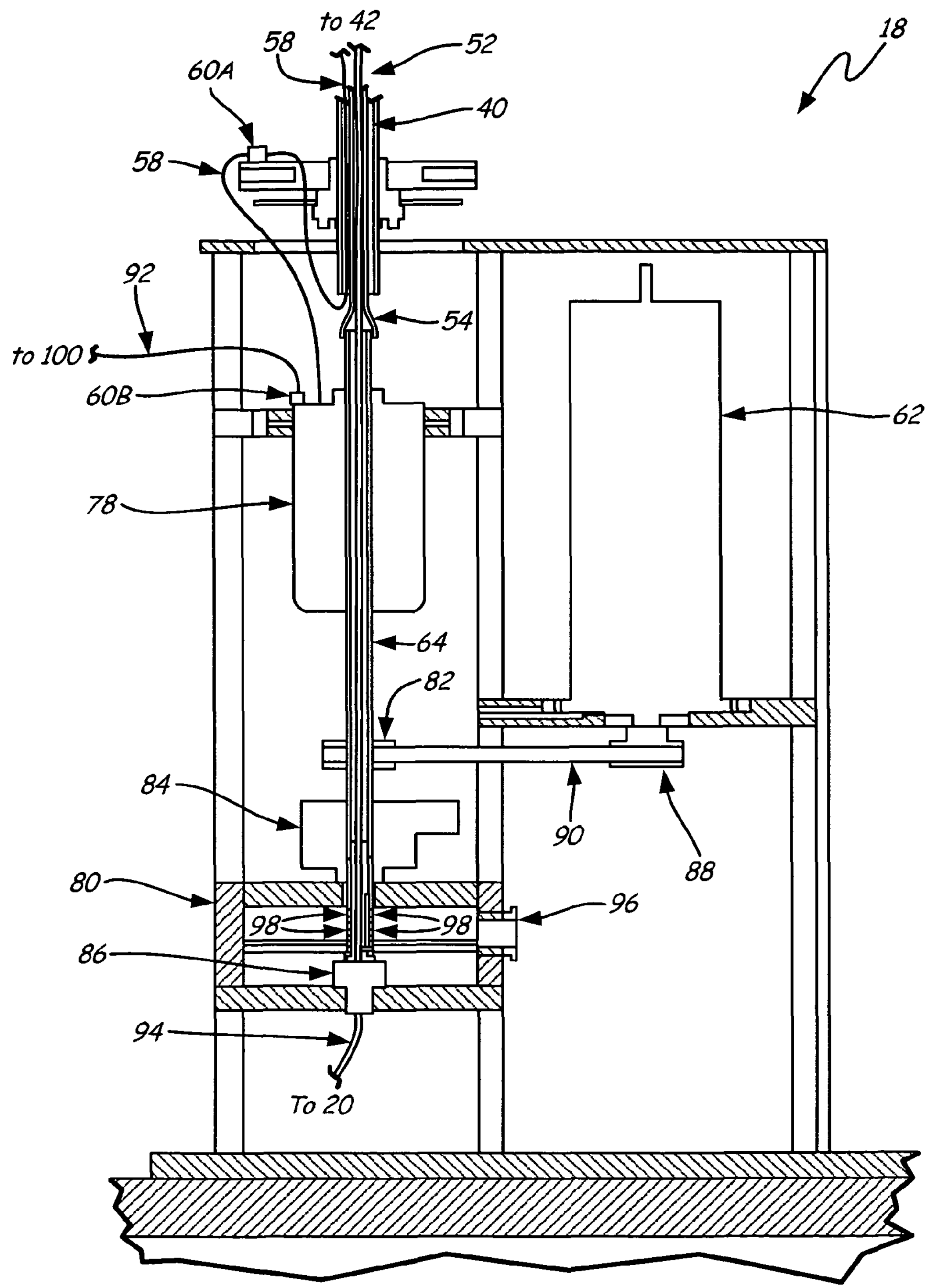
FIG. 3B is an enlarged elevation view of the lower assembly in partial cross-section.

In FIGS. 3A-3B, an enlarged view of lower assembly 18 of thermal testing assembly 10 is shown in perspective view and in elevation view in partial cross-section, respectively. Shown in FIGS. 3A-3B is lower assembly 18, bench shelf 26, first hollow shaft 40, fiber optic cable 52, slip ring wires 58, terminal blocks 60A-60B, slip ring motor 62, second hollow shaft 64, lower assembly frame 66, lower assembly top 70, lower assembly base 72, slip ring mount 74, slip ring motor mount 76, shaft aperture 77, slip ring 78, air delivery chamber 80, shaft gear 82, slip ring encoder 84; optical rotary joint 86, motor gear 88, belt 90, power wires 92, stationary cable 94, air inlet 96, and shaft holes 98.

In FIG. 3A, an enlarged view of lower assembly 18 is shown in perspective view. As stated previously, lower assembly 18 is supported by bench shelf 26. Lower assembly 18 has lower assembly frame 66, which includes lower assembly uprights 68A-68F, lower assembly top 70, lower assembly base 72, slip ring mount 74, slip ring motor mount 76, and shaft aperture 77. Lower assembly uprights 68A-68F are attached at their respective lower ends to lower assembly base 72, and lower assembly uprights 68A-68F are attached at their respective upper ends to lower assembly top 70. Lower assembly top 70 has shaft aperture 77 so that lower assembly 18 can connect to upper assembly 16, specifically first hollow shaft 40 is routed through shaft aperture 77.

Lower assembly 18 further includes slip ring motor 62, slip ring 78, and air delivery chamber 80. Slip ring 78 is attached to slip ring mount 74, which is attached to lower assembly uprights 68C-68F. Air delivery chamber 80 is also attached to lower assembly uprights 68C-68F, below slip ring 78. Slip ring motor 62 is attached to slip ring motor mount 76, which is attached to lower assembly uprights 68A-68D.

In FIG. 3B, an enlarged view of lower assembly 18 is shown in elevation view in partial cross-section. As stated previously, there are rotating components in lower assembly 18 that are substantially rotationally synchronized and substantially coaxial with the rotating components in upper assembly 16. For example, second hollow shaft 64 is substantially coaxial with first hollow shaft 40 and air distribution tube 54.

Second hollow shaft 64 is also connected to slip ring 78, shaft gear 82, slip ring encoder 84, and optical rotary joint 86. Shaft gear 82 is also connected to motor gear 88 by belt 90. Motor gear 88 is mounted to the rotor of slip ring motor 62. Because slip ring motor 62 provides rotational power to lower assembly 18, motor gear 88, belt 90, shaft gear 82, second hollow shaft 64, slip ring 78, slip ring encoder 84, and optical rotary joint 86 are rotated by slip ring motor 62. Slip ring motor 62 can be any type of electric motor, including a type of motor that is different from platform motor 44.

Second hollow shaft 64 is also connected to air distribution tube 54, which runs up through first hollow shaft 40. Although second hollow shaft 64 is substantially coaxial with air distribution tube 54 and first hollow shaft 40, exact alignment is not necessary. That is because air distribution tube 54 is flexible, allowing for some misalignment between first hollow shaft 40 and second hollow shaft 64 to be possible. Therefore, it would be advantageous for air distribution tube 54 to comprise flexible material, such suitable materials including, but not limited to, elastic rubber or plastic. In the illustrated embodiment, first hollow shaft 40 and second hollow shaft 64 are not in direct contact with one another, nor are they rigidly linked together.

Slip ring wires 58 are routed down from upper assembly 16 and are attached to a rotating portion of slip ring 78. Power wires 92 (which are depicted as a single wire for simplicity) are then connected through terminal block 60B and to a stationary portion of slip ring 78. Slip ring wires 58 are electrically connected to power wires 92 because slip ring 78 allows for electrical connections to be made between stationary components and rotating components.

Fiber optic cable 52 is routed down from upper assembly 16, through the center of second hollow shaft 64. At the bottom of second hollow shaft 64, fiber optic cable 52 is connected to optical rotary joint 86. Optical rotary joint 86 is mounted to the bottom of the inside of air delivery chamber 80. Emerging from the other side of optical rotary joint 86 is stationary cable 94, which is a stationary portion of fiber optic cable. In the illustrated embodiment optical rotary joint 86 allows fiber optic cable 52 to rotate while stationary cable 94 remains stationary. Optical rotary joint 86 transmits optical signals from testing electronics 42 (shown in FIG. 2) to testing controller 20 (shown in FIG. 1). Optical rotary joint 86 can also perform the reverse operation, transmitting optical signals from testing controller 20 to testing electronics 42. In addition, optical rotary joint 86 seals the aperture in the bottom of air delivery chamber 80, through which stationary cable 94 passes.

Near the bottom of lower assembly 18, air inlet 96 is attached to air delivery chamber 80. Air inlet 96 allows air to enter air delivery chamber 80. Air delivery chamber 80 surrounds the bottom end of second hollow shaft 64. Along the length of second hollow shaft 64 that is within air delivery chamber 80 are shaft holes 98. Shaft holes 98 allow the interior of second hollow shaft 64 to be fluidly connected to the interior of air delivery chamber 80.

Also mounted to air delivery chamber is slip ring encoder 84. Slip ring encoder 84 is additionally connected to second hollow shaft 64. The function and significance of slip ring encoder 84 will be further discussed later with FIG. 5, but slip ring encoder 84 and its corresponding mount substantially seal the aperture at the top of air delivery chamber 80, through which second hollow shaft 64 is routed, which still allowing second hollow shaft 64 to rotate.

The components and configuration of lower assembly 18 as shown in FIGS. 3A-3B allow for several things to occur. For example, the proper arrangement of lower assembly 18 components, such as slip ring 78, slip ring motor 62, and air delivery chamber 80, is provided by lower assembly frame 66. For another example, slip ring motor 62 allows for some components in lower assembly 18 to rotate with upper assembly 16. However, second hollow shaft 64 is not rigidly connected to first hollow shaft 40, but the two are only connected by mutual contact with air distribution tube 54 and slip ring wires 58. Therefore, vibrations are substantially prevented from being transmitted from lower assembly 18 to upper assembly 16. In addition, air distribution tube 54 allows for some misalignment between lower assembly 18 and upper assembly 16, and upper assembly 16 can be precision aligned independently of lower assembly 18. Therefore, lower assembly 18 does not require such precision alignment.

For another example, slip ring 78 allows for electrical connections between upper assembly 16, which rotates, and power supply 100 (not shown), which is stationary. Also, terminal block 60B (in conjunction with terminal block 60A) eases the replacement of electrical components, such as slip ring 78, without requiring complete rewiring of thermal testing assembly 10. A further example is that optical rotary joint 86 allows for a communication link to be made between upper assembly 16, which rotates, and testing controller 20, which is stationary. Fiber optic cable 52 then allows for high bandwidth communication to be made between testing electronics 42 and testing controller 20. Yet another example is that air delivery chamber 80 allows for air to enter lower assembly 18 and be fed through second hollow shaft 64 up to upper assembly 16. Because of shaft holes 98 in second hollow shaft 64, air delivery chamber 80 can remain stationary while providing air to second hollow shaft 64, which rotates.

Depicted in FIGS. 3A-3B is one embodiment of the present invention, to which there are alternative embodiments. For example, slip ring motor 62 can alternatively be connected directly to second hollow shaft 64, which can eliminate the need for shaft gear 82, motor gear 88, and belt 90. In that embodiment, slip ring motor 62 can be coaxial with second hollow shaft 64, which puts slip ring motor 62 directly above or below slip ring 78. In another example, air delivery tube can be comprised of more rigid materials, but have a flexible construction, such as a braided metal tube. For a further example, stationary cable 94 can have an electro-optical converter that converts the optical signals into electrical signals that are sent to testing controller 20. In that embodiment, the electro-optical converter also converts electrical signals from testing controller 20 to optical signals for stationary cable 94.

Figure 4:
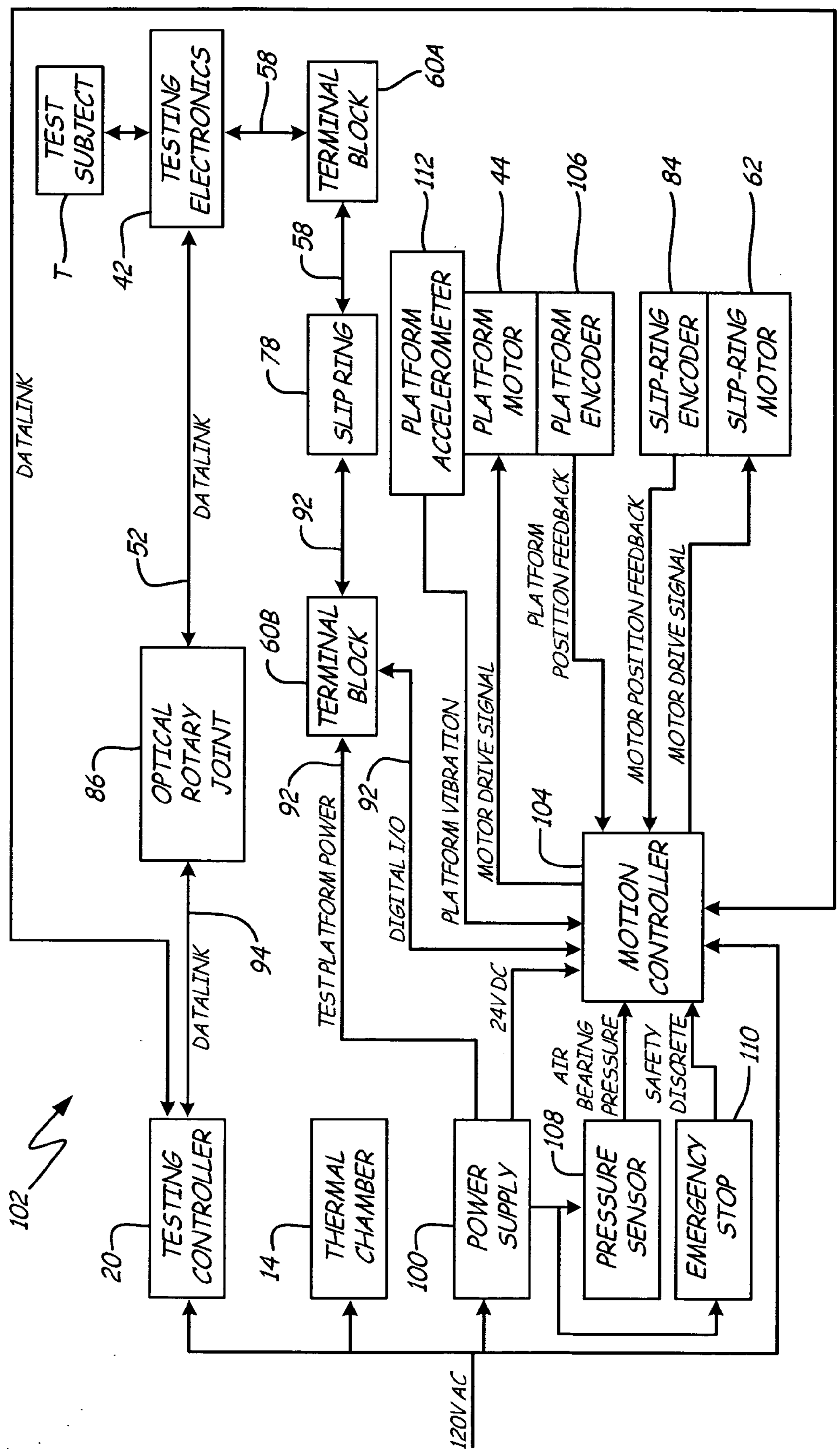
FIG. 4 is a functional electrical/optical block diagram of the thermal testing assembly.

In FIG. 4, a functional block diagram of an electrical/optical system 102 in thermal testing assembly 10 is shown. Shown in FIG. 4 are thermal chamber 14, testing controller 20, testing electronics 42, platform motor 44, fiber optic cable 52, slip ring wires 58, terminal blocks 60A-60B, slip ring motor 62, slip ring 78, slip ring encoder 84, power wires 92, stationary cable 94, power supply 100, electrical/optical system 102, motion controller 104, platform encoder 106, pressure sensor 108, emergency stop 110, platform motor accelerometer 112, and test subject T.

Thermal chamber 14, testing controller 20, power supply 100, and motion controller 104 all receive electrical power from a 120 Volt alternating current (AC) source, such as a wall outlet. Power supply 100 supplies 24 Volt direct current (DC) electrical power to testing electronics 42 and test subject T through power wires 92, slip ring 78, and slip ring wires 58. Power wires 92 have terminal block 60B and slip ring wires 58 have terminal block 60B. Terminal blocks 60A-60B allow for changing of the wiring arrangement without having to rewire thermal testing assembly 10.

Because of the electrical, optical, and pneumatic lines that are physically attached to both upper assembly 16 and lower assembly 18, it is advantageous to substantially synchronize platform motor 44 and slip ring motor 62 in a master/slave fashion. Such synchronization can be done during all phases of operation, including acceleration, steady state, and deceleration. Synchronization can be accomplished electronically, for example, through the use of a single motion controller 104, which controls both platform motor 44 and slip ring motor 62. In order to assist in synchronization two encoders are used. Platform encoder 106 and slip ring encoder 84 can measure the position, angular velocity, and/or angular acceleration of first hollow shaft 40 and second hollow shaft 64, respectively. The outputs from platform encoder 106 and slip ring encoder 84 are then fed into motion controller 104 to provide feedback for use in synchronizing platform motor 44 and slip ring motor 62.

In addition, testing controller 20, pressure sensor 108, emergency stop 110, and platform motor accelerometer 112 can also provide information to motion controller 104. Generally, testing controller 20 controls motion controller 104. Specifically, pressure sensor 108 indicates whether there is sufficient air pressure available to support the air bearing rotor in platform motor 44, and if there is not, then motion controller 104 will not rotate platform motor 44 and slip ring motor 62. On the other hand, emergency stop can indicate that the user does not want platform motor 44 and/or slip ring motor 62 to operate, such as for safety reasons. Platform motor accelerometer 112 is affixed to the stationary portion of platform motor 44 and indicates vibrations due to an imbalance in the rotating components of upper assembly 16 during rotational operation.

In the illustrated embodiment, testing controller 20 optically connected to testing electronics 42 via stationary cable 94, optical rotary joint 86, and fiber optic cable 52. Testing electronics 42 are electrically connected to test subject T, with test subject T being, for example, an angular velocity or acceleration sensor. Testing controller 20 can send signals to and collect data from test subject T because testing electronics 42 can convert the optical signals from testing controller 20 into electrical signals for test subject T. In addition, testing electronics 42 can convert electrical signals from test subject T into optical signals for testing controller 20, so that testing controller 20 can analyze the output of test subject T.

The components and configuration of electrical/optical system 102 allow the electrical components of thermal testing assembly 10 to receive power and for data to be transmitted throughout thermal testing assembly 10. In addition, electrical/optical system 102 allows for platform motor 44 to be synchronized with slip ring motor 62, and for the incorporation of safety measures in thermal testing assembly 10.

Depicted in FIG. 4 is one embodiment of the present invention, to which there are alternative embodiments. For example, motion controller 104 can also communicate with testing electronics 42 and test subject T through power wires 92, slip ring 78, and slip ring wires 58. However, it is preferable to use low rate communications and/or simple digital on/off signals when communicating through this channel due to the possibility of signal quality reduction due to slip ring 38. In another example, testing controller 20 and testing electronics 42 can be connected in alternative ways, such as by a wireless (radio frequency) connection. In such an embodiment, a radio antenna would be connected to testing electronics 42 and another radio antenna would be placed in an aperture in the side of thermal housing 28. The latter radio antenna would then be connected to testing controller 20.

For a further example, test subject T can comprise more than merely a sensor. Test subject T can be a sensor with its own control electronics; a final packaged product or multiple products (for example, cell phones); or any other combination of sensor architecture. Testing electronics 42 and testing controller 20 can be adapted to the degree of components and capabilities that comprise test subject T (and the support required by test subject T), such that meaningful testing, calibration, or characterization can be carried out. Furthermore, testing electronics 42 can perform varying degrees of output analysis from test subject T. Testing electronics 42 and testing controller 20 can be adapted to the desired degree of data analysis that each component does such that testing, calibration, or characterization of test subject T can be carried out.

Figure 5:
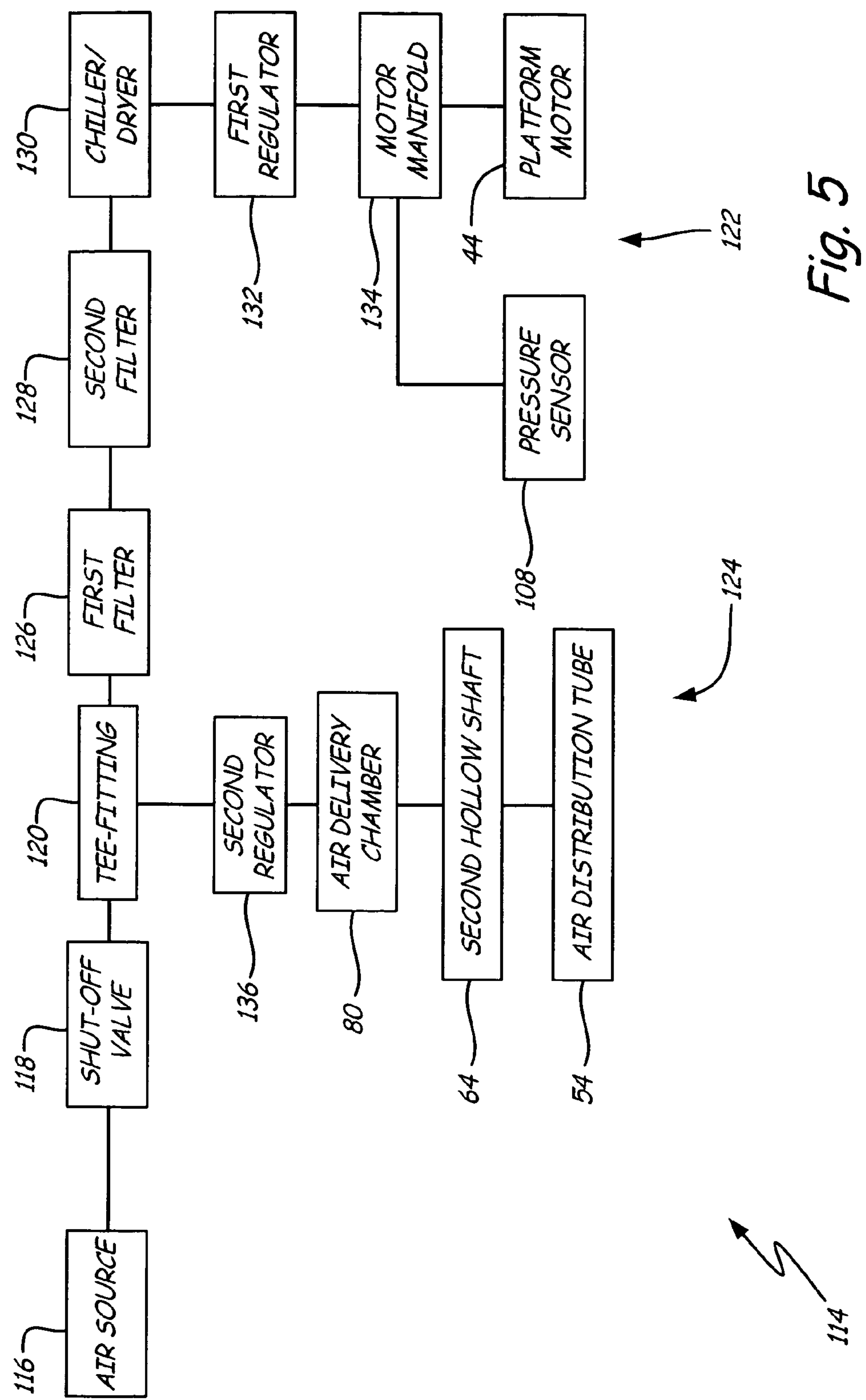
FIG. 5 is a functional pneumatic block diagram of the thermal testing assembly.

In FIG. 5, is a functional block diagram of a pneumatic system 114 in a thermal testing assembly 10 is shown. Shown in FIG. 5 are platform motor 44, air distribution tube 54, second hollow shaft 64, air delivery chamber 80, pressure sensor 108, pneumatic system 114, air source 116, shut-off valve 118, tee fitting 120, motor branch 122, platform branch 124, first filter 126, second filter 128, chiller/dryer 130, first regulator 132, motor manifold 134, and second regulator 136.

Air source 116 provides air to thermal testing assembly 10, and air source 116 can be any suitable pressurized source, for example a pressurized tank, a compressor, or a facility air supply (i.e. "shop air"). Air source 116 is connected to shut-off valve 118 and then to tee fitting 120. Attached to tee fitting 120 are two pathways—motor branch 122 and platform branch 124.

Motor branch 122 has first filter 126, second filter 128, chiller/dryer 130, first regulator 132, motor manifold 134, pressure sensor 108, and platform motor 44. While first filter 126 is preferably a 5 micron filter and second filter 128 is preferably a 0.01 micron filter, both filters remove contamination from air. Chiller/dryer 130 cools and removes moisture from the air, and first regulator 132 controls the pressure of the air. After the preparation of the air, motor branch 122 has motor manifold 134 for distributing the air to both pressure sensor 108 and platform motor 44. Pressure sensor 108 monitors the pressure of the air at motor manifold 134, while platform motor 44 uses the air to support the air bearing rotor that rotates inside platform motor 44.

Platform branch 124 of pneumatic system 114 has second regulator 136, air delivery chamber 44, second hollow shaft 64, and air distribution tube 54. Second regulator 136 controls the pressure of the air in platform branch 124. As stated previously, the interiors of air distribution tube 54, second hollow shaft 64, and air delivery chamber 80 form a conduit for air to reach testing electronics 42.

The components and configuration of pneumatic system 114 allow for platform motor 44 to operate using an air bearing rotor. In addition, because the temperature of the air can be independent of thermal testing assembly 10, the air will transfer heat to or from thermal testing assembly 10 if there exists a temperature differential between them. Specifically this allows for testing electronics 42 (underneath a thermally insulating housing, as shown in FIGS. 6A-6B) to be cooled or heated by the air and thereby maintained within standard operating temperatures that are independent of the temperature inside thermal cavity 32.

Depicted in FIG. 5 is one embodiment of the present invention, to which there are alternative embodiments. For example, as stated with FIG. 2, air distribution tube 54 can be connected to a manifold that can distribute air specifically on or about testing electronics 42. For another example, air can be routed from air distribution tube 54 to power pneumatic components that are attached to platform 36 (not shown).

Figures 6A, 6B:
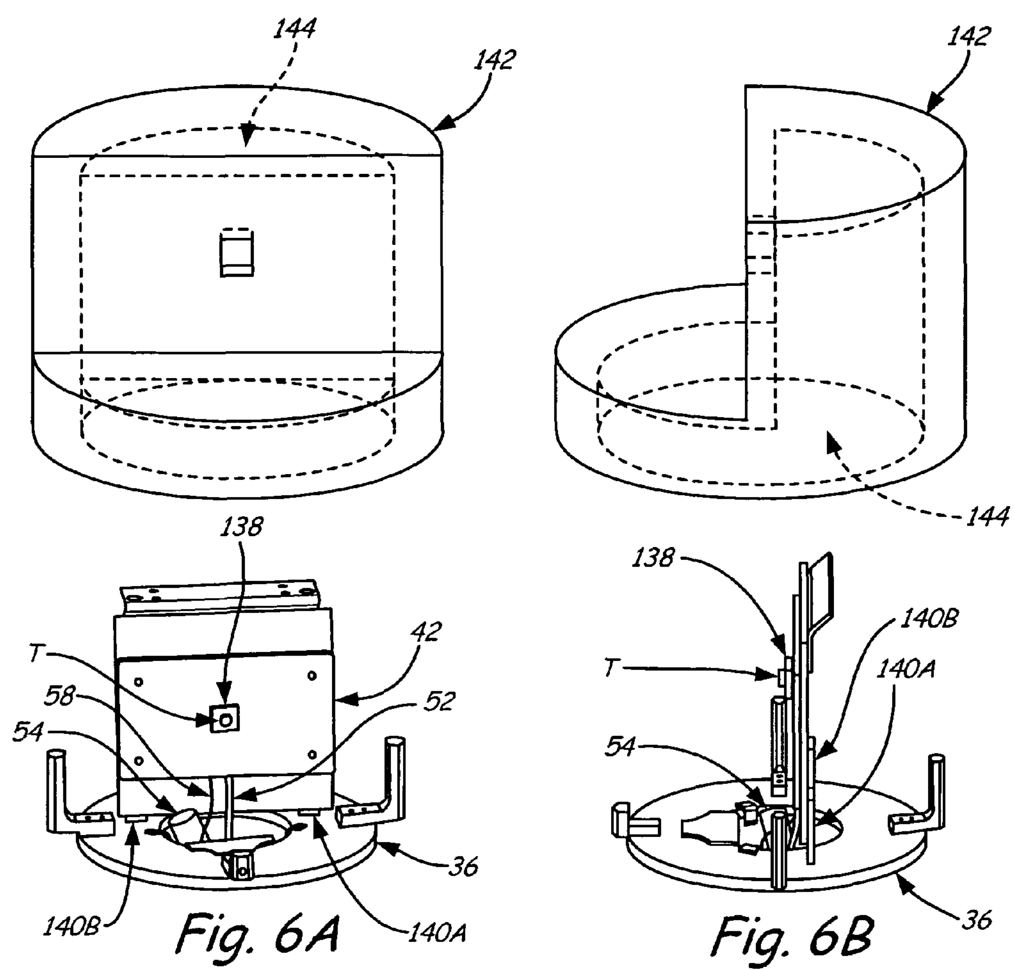
FIGS. 6A and 6B are an exploded front and side perspective views, respectively, of components connected to a platform of the thermal testing assembly for single axis testing.

In FIGS. 6A-6B, an exploded perspective view of components connected to platform 36 of thermal testing assembly 10 is shown. Shown in FIGS. 6A-6B is platform 36, testing electronics 42, air distribution tube 54, socket 138, posts 140A-140B, platform cover 142, platform cavity 144, and test subject T.

FIG. 6A is an exploded, front perspective view of components connected to a platform of a thermal testing assembly. Test subject T is connected to testing electronics 42 via socket 138. Test electronics 42 are attached to posts 140A-140B, which are attached to platform 36. As stated previously with FIG. 1, there is normally a housing or shroud attached to the top of platform 36, that housing or shroud being platform cover 142. In the illustrated embodiment, testing electronics 42 fit inside platform cavity 144. However, test subject T projects out of an aperture in platform cover 142 into thermal cavity 32.

Platform cover 142 can insulate testing electronics 42 from the temperatures inside thermal cavity 32 while still exposing test subject T to them. Because platform cover 142 is an insulator, platform cover 142 is preferably comprised of thermally insulating material, for example, expanded polystyrene. Furthermore, air distribution tube 54 distributes air within platform cover 142. Because of the insulating properties of platform cover 142, the air from air distribution tube 54 can maintain testing electronics 42 at an independent temperature from that of thermal cavity 32 and test subject T.

FIG. 6B is an exploded, side perspective view of components connected to a platform of a thermal testing assembly. In the illustrated embodiment, testing electronics 42 is a circuit board. In order to aid in the insulation of testing electronics 42 from the thermal extremes in thermal cavity 32, the electronic components are located on the side of testing electronics 42 opposite from socket 138 and test subject T. In addition, to further aid in the insulation of testing electronics 42, there is a seal (not shown) between platform cover 142 and the bottom of thermal cavity 32 (not shown), and also beneath platform 36. While the seal does not contact platform 36 or platform cover 142, the seal requires thermal energy from thermal cavity 32 to travel in a multidirectional path to enter the insulated area of testing electronics 42. Such a path extends inwards toward the opening in bottom of thermal cavity 32, then upwards between the seal and platform cover 142 while platform cover 142 is rotating, thus creating an adverse pressure field. This complex path in an adverse pressure field substantially reduces the amount of thermal transfer to platform cavity 144. Also, in the illustrated embodiment platform cover 142 is substantially cylindrical in shape. Such a shape is beneficial to the aerodynamic properties of platform cover 142 as platform 36 is rotated at high speeds.

The components and configuration of platform 36 as shown in FIGS. 6A-6B allow testing electronics 42 to be maintained within standard operating temperatures due to the pneumatic system of thermal testing assembly 10. When combined with the ability to control the temperature inside thermal cavity 32, test subject T to be tested, calibrated, or characterized at varying temperatures without the varying temperature affecting testing electronics 42. This reduces the need to compensate for the temperature-dependent characteristics of testing electronics 42.

Depicted in FIGS. 6A-6B is one embodiment of the present invention, to which there are alternative embodiments. For example, platform cover 142 can be completely cylindrical, with another cavity starting at the top of platform cover 142 and extending past the aperture for test subject T. In that embodiment, test subject T is exposed to thermal cavity 32, testing electronics 42 are insulated from thermal cavity 32, and platform cover 142 has a cylindrical exterior.

Figure 7A:
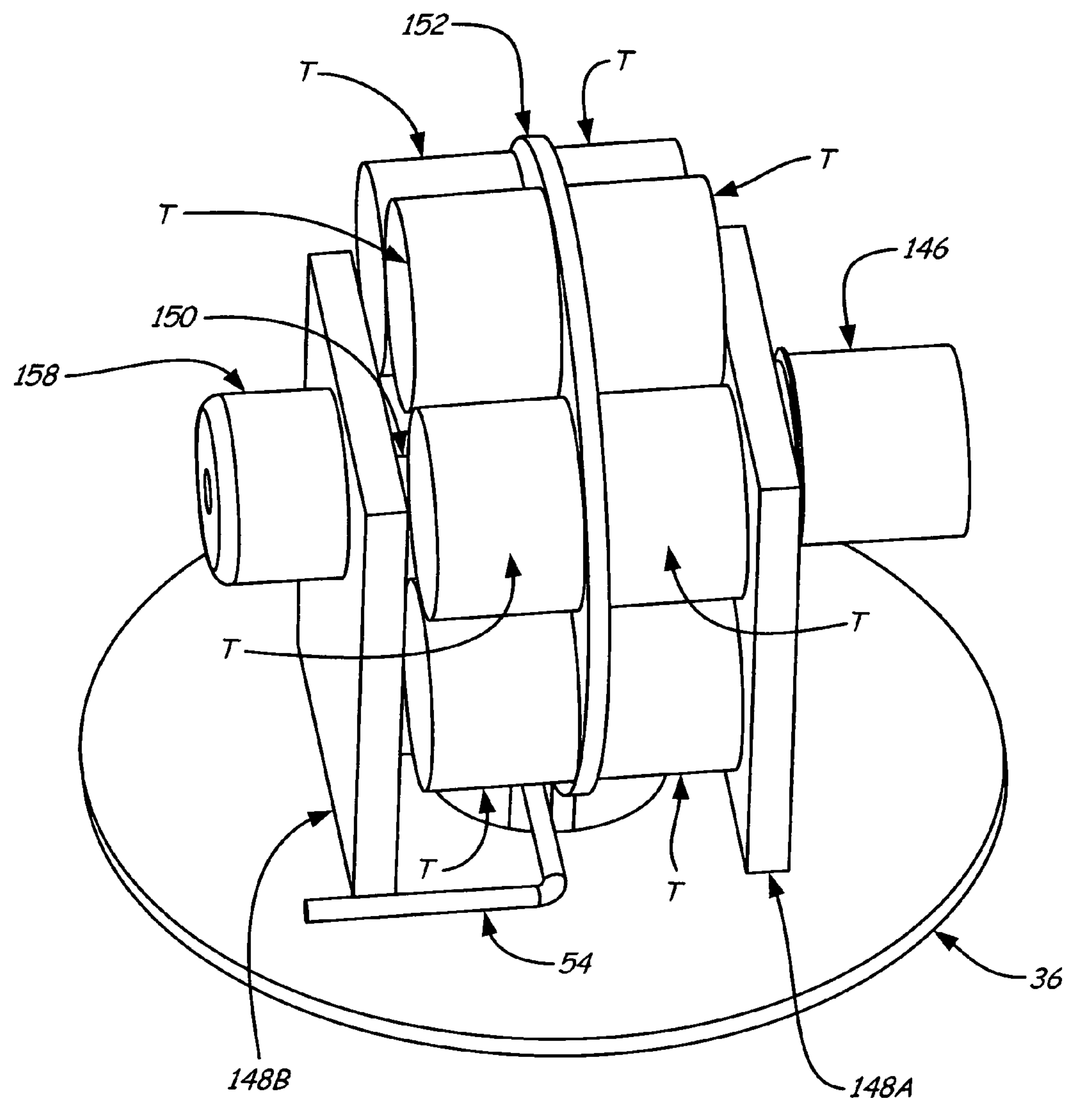
FIG. 7A is a perspective view of an apparatus for multiaxis testing using the thermal testing assembly with a cover removed.
Figure 7B:
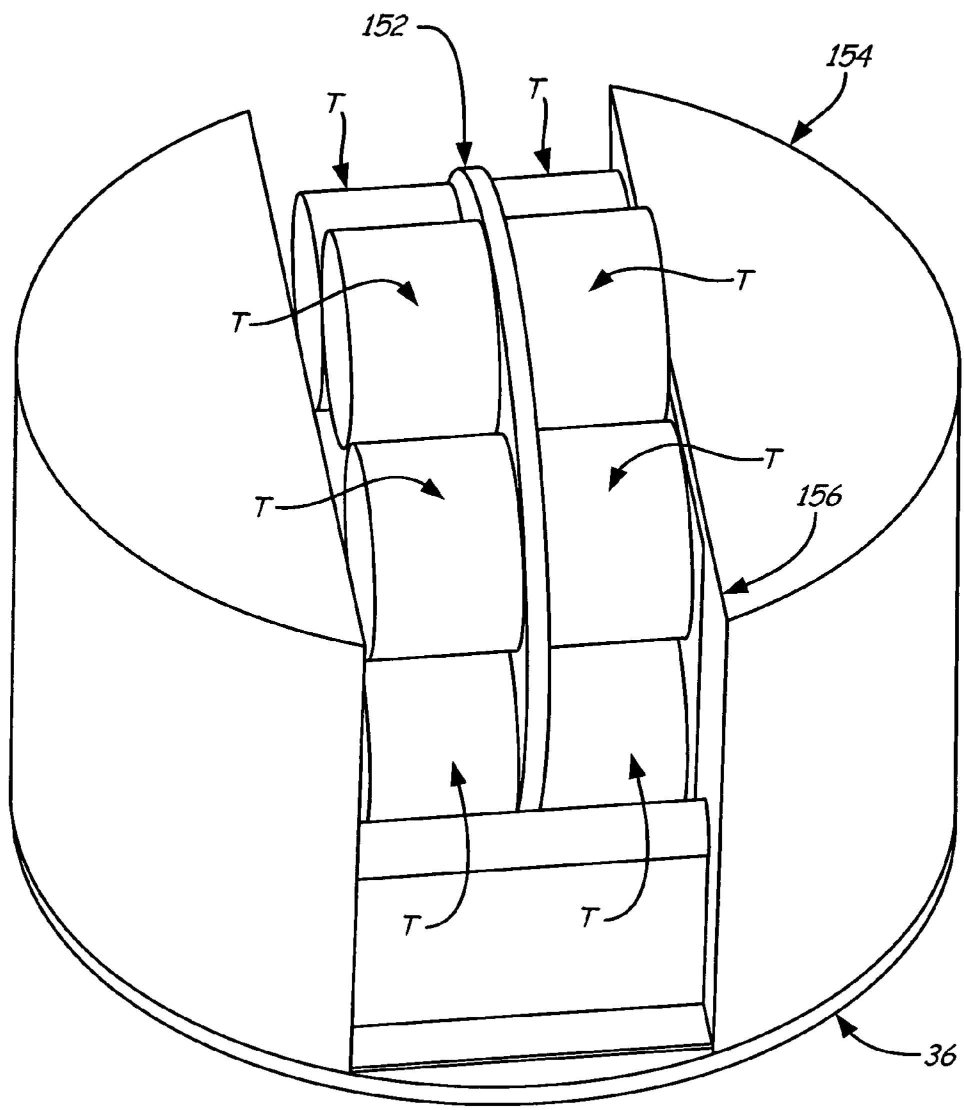
FIG. 7B is a perspective view of an apparatus for multiaxis testing using the thermal testing assembly with a cover installed.

In FIGS. 7A-7B, a perspective view of an apparatus for multiaxis testing using thermal testing assembly 10 is shown. Shown in FIGS. 7A-7B is platform 36, multiaxis motor 146, multiaxis shaft supports 148A-148B, multiaxis shaft 150, multiaxis platform 152, multiaxis cover 154, multiaxis cavity 156, multiaxis slip ring 158, and a plurality of test subjects T. However, in an alternative embodiment, there can be only a single test subject T.

FIG. 7A is a perspective view of an apparatus for multiaxis testing using a thermal testing assembly. In the illustrated embodiment, multiaxis motor 146 and multiaxis shaft support 148 are attached to platform 36. Multiaxis shaft 150 is connected to the rotor of multiaxis motor 146 and is rotatably connected to multiaxis shaft supports 148A-148B. Located on multiaxis shaft 150, between multiaxis motor 146 and multiaxis shaft support 148, is multiaxis platform 152. Multiaxis motor 146 can rotate multiaxis platform 152, and test subjects T are mounted to both sides of multiaxis platform 152. Test subjects T are electrically connected through multiaxis slip ring 158.

In order to use thermal testing assembly 10 for multiaxis testing, both axes created by first hollow shaft 40 and multiaxis shaft 150 are used. Specifically, one shaft can be fixed while the other shaft is rotated so that test subject T can be tested along multiple axes, and the then the opposite arrangement can be used to test along the remaining axes. Finally, both shafts can be rotated so that test subject T can be tested under multiple input conditions.

FIG. 7B is a perspective view of an apparatus for multiaxis testing using a thermal testing assembly. In the illustrated embodiment, platform 36 has multiaxis cover 154. Multiaxis cover is shaped such that test subjects T are exposed to thermal chamber 14, while other components attached to platform 36, such as multiaxis motor 146, are insulated from thermal cavity 32. Specifically, test subjects T are positioned in multiaxis cavity 156, which is exposed to thermal cavity 32. Also, in the illustrated embodiment multiaxis cover 154 is substantially cylindrical in shape. Such a shape is beneficial to the aerodynamic properties of multiaxis cover 154 as platform 36 is rotated at high speeds.

The components and configuration of an apparatus as shown in FIGS. 7A-7B allow for multiaxis rotational testing of test subject T under varying temperature conditions. In addition, test subject T is exposed to thermal cavity 32 while other components are insulated from thermal cavity 32. Because of the pneumatic system of thermal testing assembly 10, the insulated components can be maintained within standard operating temperatures due. When combined with the ability to control the temperature inside thermal cavity 32, test subject T to be tested, calibrated, or characterized at varying temperatures without the varying temperature affecting other components on multiaxis platform 152.

It should be recognized that the present invention provides numerous benefits and advantages. For example, having first hollow shaft 40 and second hollow shaft 64 separated means that lower assembly 18 does not need to be precision aligned. In addition, upper assembly 16 does not need to be realigned when lower assembly 18 has been disassembled for maintenance. Also, any vibration caused by lower assembly 18 is isolated from upper assembly 16, increasing the fidelity of the testing, calibration, or characterization results. Because slip ring 38 is rotated by slip ring motor 62, platform motor 44 can have an air bearing due to the decreased motor power and radial loads. Such an air bearing can require little maintenance over a long useful life, while minimizing vibrations from platform motor 44 to platform 36. This allows for testing over the course of years, allowing the testing of whether test subject T changes its response over time when exposed to a controlled temperature.

Another example of the benefits and advantages of the invention is that having testing electronics 42 inside thermal chamber 14 means that signals from test subject T do not have to go through slip ring 78, where they can lose fidelity. In addition, the ability to independently control the temperature of platform cavity 144 allows for testing electronics 42 to be used at standard operating temperatures, extending their useful life and eliminating the need for non-standard electronic equipment. It also allows for testing, calibration, or characterization of test subject T without needing to compensate for the thermal characteristics of testing electronics 42 over various temperatures.

Yet another example of the benefits and advantages of the invention is that shaft holes 98 allow for second hollow shaft 64 to be connected with air delivery chamber 44 without requiring a traditional pneumatic or hydraulic rotating swivel joint. In the embodiment having multiaxis platform 152, testing, calibration, or characterization of three axes of test subject T can be completed without thermal chamber 14 being opened or test subject T being repositioned by a human operator. More generally, the ability to rotate test subject T without rotating thermal chamber 14 reduces energy consumption, allows for significantly higher rotational velocity and acceleration testing, and has fewer safety risks.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A testing system for testing, calibrating, or characterizing an electronic test subject while rotating the test subject within a thermally controlled chamber, the system comprising:

a stationary thermal chamber;

a test subject;

testing electronics that receive electronic data from the test subject;

a rotatable platform inside the thermal chamber to which both the test subject and the testing electronics are mounted; and a platform cover for the rotatable platform that rotates with the rotatable platform, and exposes the test subject to the temperature inside the thermal chamber and insulates the testing electronics from the temperature inside the thermal chamber.

2. The testing system of claim 1, and further comprising:

a pneumatic system that delivers gas to the testing electronics, the testing electronics being inside the platform cover, the gas being at a temperature independent of the temperature inside the thermal chamber.

3. The testing system of claim 1, and further comprising:

a platform motor that rotates the rotatable platform; and a slip ring motor that rotates a slip ring through which electrical power is provided to the testing electronics.

4. The testing system of claim 3, wherein a first shaft connected to the platform motor and a second shaft connected to the slip ring motor are substantially concentric.

5. The testing system of claim 4, and further comprising:

a motion controller for substantially synchronizing the platform motor and the slip ring motor.

6. The testing system of claim 5, and further comprising:

a pneumatic system that delivers gas to the testing electronics, the testing electronics being inside the platform cover, the gas being at a temperature independent of the temperature inside the thermal chamber.

7. The testing system of claim 6, wherein the pneumatic system delivers gas through a gas distribution tube inside of a hollow inside of the first shaft, and a hollow inside of the second shaft with the gas distribution tube being connected to the second shaft.

8. The system of claim 7, wherein the gas delivery tube is comprised of flexible and elastic material.

9. The system of claim 8, and further comprising:

a gas delivery chamber that surrounds a portion of the second hollow shaft, the portion of the second hollow shaft having holes in it such that gas can flow from the gas delivery chamber into the hollow inside of the second shaft.

10. The system of claim 3, wherein the platform motor includes an air bearing.

11. The system of claim 5, wherein the first motor and the second motor are controlled by a common controller.

12. A method of operating a testing system for testing, calibrating, or characterizing an electronic test subject, the method comprising:

controlling the temperature inside a stationary thermal chamber;

mounting a test subject on a rotatable platform, the test subject and the rotatable platform being inside the thermal chamber;

covering the rotatable platform with a platform cover that rotates with the rotatable platform and that exposes the test subject to the temperature inside the thermal chamber;

rotating the platform;

testing the test subject using testing electronics that are mounted on the platform inside the thermal chamber, the testing electronics receiving electronic data from the test subject; and insulating thermally the testing electronics from the thermal chamber with the platform cover.

13. The method of claim 12, and further comprising:

controlling the temperature of the testing electronics independently from the temperature inside the thermal chamber.

14. The method of claim 12, and further comprising:

rotating the platform with a first shaft that is rotated by a platform motor;

providing the testing electronics with electrical power through a slip ring; and rotating a portion of the slip ring with a second shaft that is rotated by a slip ring motor.

15. The method of claim 14, and further comprising:

synchronizing the rotation of the platform motor and the slip ring motor.

16. The method of claim 14, and further comprising:

isolating the first shaft from vibrations in the second shaft.

17. The method of claim 14, wherein the platform motor includes an air bearing.

18. The method of claim 12, and further comprising:

controlling the testing with a testing controller that is stationary and outside of the thermal chamber.

19. The method of claim 12, wherein the test subject comprises an angular velocity measurement device or an acceleration measurement device.

20. The method of claim 12, wherein testing includes at least one of calibration or characterization of the test subject.

* * * * *